United States Patent [19]

Franz

[11] 4,260,561
[45] Apr. 7, 1981

[54] PROCESS FOR THE PREPARATION OF CARBONYL DIFLUORIDES

[75] Inventor: Raimund Franz, Kelkheim, Fed. Rep. of Germany

[73] Assignee: Hoechst Aktiengesellschaft, Frankfurt am Main, Fed. Rep. of Germany

[21] Appl. No.: 43,736

[22] Filed: May 30, 1979

[30] Foreign Application Priority Data

Jun. 1, 1978 [DE] Fed. Rep. of Germany ....... 2823981

[51] Int. Cl.³ .................. C07C 51/04; C07C 51/58
[52] U.S. Cl. ................................................. 260/544 F
[58] Field of Search ........................................ 260/544F

[56] References Cited

U.S. PATENT DOCUMENTS

| 2,836,622 | 5/1958 | Tullock | 260/544 F |
| 3,088,975 | 5/1963 | Fawcett et al. | 260/544 F |
| 3,253,029 | 5/1966 | Fawcett | 260/544 F |

*Primary Examiner*—Natalie Trousof
*Assistant Examiner*—L. Hendriksen
*Attorney, Agent, or Firm*—Curtis, Morris & Safford

[57] ABSTRACT

Carbonyl difluorides of the formula $$F-(CO)_n-F,$$

in which n is 1 (difluorophosgene) or 2 (oxalyl fluoride), are prepared by fluorination of the corresponding carbonyl dichlorides (phosgene, oxalyl chloride) with HF in the presence of $CH_3CN$ and optionally also of a tertiary amine which binds HCl.

9 Claims, No Drawings

PROCESS FOR THE PREPARATION OF CARBONYL DIFLUORIDES

The present invention relates to a process for the preparation of carbonyl difluorides.

Difluorophosgene and oxalyl fluoride, which are carbonyl difluorides, are valuable starting compounds for the preparation of fluoro-organic compounds, such as halogenated methanes (cf. Beilstein E IV 3, page 21) or of perfluorinated ethers (U.S. Pat. No. 3,250,807).

It is already known to prepare difluorophosgene and oxalyl fluoride by way of fluorination of the corresponding dichlorides (phosgene and oxalyl chloride). As fluorinating agents there are used in most cases alkali metal fluorides, especially NaF (J. Org. Chem. 1960, No. 25, at pages 2016-19; U.S. Pat. No. 3,088,975), which may be employed either in a heterogeneous form as a suspension in an appropriate aprotic medium or—in the case of the preparation of difluorophosgene—also at high temperatures in a melted form.

The fluorination in the heterogeneous system has the drawback, however, that the grain size and the degree of dryness of the fluoride considerably influence the course of the reaction; besides, reactions in the heterogeneous system proceed generally at a lower rate than reactions in homogeneous systems, so that higher temperatures are required in order to arrive at suitable reaction times. However, in the case of thermally unstable substrates or products such as oxalyl fluoride, elevated temperatures are unfavorable. Thus, according to the state of the art, the preparation of oxalyl fluoride by fluorination of oxalyl chloride with alkali metal fluorides at a temperature of up to about 120° C. always yields fluorophosgene as an undesirable by-product.

Fluorinating with melted alkali metal fluoride to prepare oxalyl fluoride is not possible due to the thermal instability of the latter. This method may only be considered for the preparation of difluorophosgene which is more stable thermally. In this case suitable apparatus which is resistant to heat and corrosion is required.

It has also been known to obtain carboxylic acid fluorides from the corresponding carboxylic acid chlorides by fluorination with hydrogen fluoride (Houben-Weyl, Methoden der Organischen Chemie, 4th edition, vol. V/3, published by G. Thieme, Stuttgart 1962, pages 119 et seq.). Hydrogen fluoride is indeed a considerably less expensive fluorinating agent than alkali metal fluorides; however, it can only be used with difficulty for the preparation of difluorophosgene from phosgene, and practically cannot be used at all for the preparation of oxalyl fluoride from oxalyl chloride.

In order to prepare difluorophosgene from phosgene and hydrogen fluoride, a temperature of from 140° to 150° C. must be applied in an iron autoclave in the presence of active charcoal (Beilstein E III 3, page 22).

The fluorination of oxalyl chloride with hydrogen fluoride is infeasible because there is practically no reaction when mixing the reactants, and decomposition occurs at elevated temperatures.

It has therefore been a desirable object and a task to be solved to find an improved process for the preparation of difluorophosgene and oxalyl fluoride.

Said task was solved in accordance with the invention by fluorination of phosgene and/or oxalyl chloride with hydrogen fluoride in the presence of acetonitrile.

The subject of the invention is therefore a process for the preparation of carbonyl difluorides of the formula

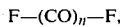

$$F-(CO)_n-F,$$

in which n is 1 or 2, by fluorination of the corresponding carbonyl dichlorides, which comprises carrying out the fluorination with hydrogen fluoride in the presence of acetonitrile.

If in the above formula n represents 1, difluorophosgene is involved, and if n is 2, the compound involved is oxalyl fluoride. In order to prepare difluorophosgene, the starting compound to be used is phosgene $COCl_2$, whereas for the preparation of the oxalyl fluoride there is to be employed oxalyl chloride $(CO)_2Cl_2$ as the starting compound. It goes without saying that the corresponding bromine compounds (dibromophosgene and/or oxalyl bromide) might also be used as starting compounds; however, no advantage is involved in this variant, since the bromides are more expensive and less stable thermally than the chlorides. The amount of hydrogen fluoride to be employed should be at least equal to the theoretical amount, i.e. at least 2 mols per mol of carbonyl difluoride; however, preference is given to a molar excess amount of from about 50 to 200 mol %.

In order to carry out the reaction successfully, the presence of rather small amounts of acetonitrile is sufficient; it is preferred, however, to effect the fluorination in a mixture of hydrogen fluoride and acetonitrile in which the hydrogen fluoride concentration is in the range of from about 10 to 99, preferably from about 30 to 40 mol %.

If the concentration of hydrogen fluoride in said mixture does not exceed 50 mol %, the reaction may also be carried out in an apparatus of borosilicate glass.

The surprisingly favorable reaction progress is probably due partly to the particular solubilizing properties and partly to the special basicity of the acetonitrile.

A favorable temperature for the fluorination of the invention is in the range of from about 0° to 50° C., preferably from about 10° to 40° C.

Upon completion of the reaction, the reaction product is worked up suitably by distillation, optionally under reduced pressure.

In the case of the fluorination of oxalyl chloride, the gas mixture being developed consists of hydrogen fluoride and oxalyl fluoride, the latter being easy to extract by condensation with the aid of cooling traps due to the level of its boiling and/or melting point.

In the case of the fluorination of phosgene, the product mixture consists of difluorophosgene and hydrogen chloride which can only be separated by a complicated fractionation or a subsequent chemical reaction with a suitable acid-binding agent. A preferred variant of the process according to the invention therefore involves carrying out the fluorination in the presence of an auxiliary base which binds hydrogen chloride, the base neither reacting with the substrate nor with the reaction product. Preferred auxiliary bases of this kind are tertiary amines, especially triethylamine. The amount of the auxiliary base to be employed should be in a range that the total hydrogen chloride being formed is bound. By working up the hydrochloride obtained by means of a lye, the auxiliary base may be recovered quantitatively.

According to the process of the invention, difluorophosgene and/or oxalyl fluoride are obtained in a yield of more than 70% of the theory. As compared with the processes of the state of the art, the above-described process involves the advantage that the fluorination may be carried out with an inexpensive fluorinating agent in a simple manner—if desired, in glass vessels—under conditions which do not favor the formation of by- and/or decomposition products. In contradistinction to the process described in literature, no undesirable fluorophosgene can be detected in the product mixture being formed in the preparation of oxalyl fluoride.

The following Examples serve to further illustrate the invention.

EXAMPLE 1

A mixture of 120 g of hydrogen fluoride (6 mols) and about 500 g of acetonitrile is placed into a stirring flask of borosilicate glass having a capacity of 2 liters, and 202 g of triethylamine (2 mols) are added dropwise, while cooling. 99 Grams of phosgene (1 mol) are slowly added to the solution thus obtained at room temperature. On the stirring flask there has been provided a reflux condenser which is charged with a dry ice freezing mixture. The difluorophosgene being formed passes through the condenser and is condensed in a subsequent trap charged with liquid air. The reaction is completed by applying a vacuum and heating the reaction mixture up to a maximum of 40° C. Thereafter, the cooling trap contains about 60 g of crude product which according to the IR spectrum and gas chromatography shows only from 15 to 20% of carbon dioxide as impurity. Thus, the yield is about 72% of the theory.

EXAMPLE 2

At 10° C. 99 g of phosgene (1 mol) were added to a solution of 60 g of hydrogen fluoride (3 mols) in about 250 g of acetonitrile being present in a 1-liter stirring flask of borosilicate glass provided with a reflux condenser ($-78°$ C.). Stirring was continued for 2 hours at room temperature, and the reaction mixture was brought to a gentle boil for 3 hours by reducing the pressure. In a trap arranged behind the reflux condenser and filled with liquid air, 60 g of a mixture were collected which according to the IR spectrum contained hydrogen chloride and difluorophosgene as the main components, as well as carbon dioxide and fluorochlorophosgene as secondary components.

EXAMPLE 3

A solution of 120 g of hydrogen fluoride (6.0 mols) in 600 ml of acetonitrile is introduced into a stirring vessel of borosilicate glass consisting of a flask, a reflux condenser (with a brine of $-10°$ C.) and three cooling traps arranged in sequence in a bath of dry ice, and at about 15° C., 254 g of oxalyl chloride (2.0 mols) are added dropwise within 1 hour. During this time and during the subsequent stirring period of 1 hour, a slight gas development can already be observed, which is subsequently intensified by applying a vacuum (water-jet vacuum pump). Depending on the gas development observed, the internal pressure is reduced to 60–70 mbars within about 2 hours, while reducing the temperature of the cooling brine from $-10°$ to $-40°$ C. The end of the reaction becomes obvious by the cessation of the gas development. The condensates present in the cooling traps are combined and subjected to a fractionation. In this manner, from 130 to 140 g of oxalyl fluoride having a boiling point of $-2°$ C. are obtained (=69 to 74% of the theory).

What is claimed is:

1. A process for the preparation of a carbonyl difluoride of the formula $$F-(CO)_n-F$$

in which n is 1 or 2, which comprises fluorinating the corresponding carbonyl dichloride with hydrogen fluoride in the presence of acetonitrile.

2. A process as claimed in claim 1, which comprises fluorinating in a mixture of hydrogen fluoride and acetonitrile in which the concentration of hydrogen fluoride is in the range of from about 10 to 99 mol%.

3. A process as claimed in claim 2, wherein the concentration of hydrogen fluoride is in the range of from about 30 to 40 mol%.

4. A process as claimed in claim 1, 2 or 3, which comprises fluorinating at a temperature of from about 0° to 50° C.

5. A process as claimed in claim 4, wherein the temperature is from about 10° to 40° C.

6. A process as claimed in claim 5, wherein the carbonyl dichloride is phosgene.

7. A process as claimed in claim 1, 2, or 3, which comprises fluorinating in the presence of a tertiary amine which binds hydrogen chloride.

8. A process as claimed in claim 7, wherein the tertiary amine is triethylamine.

9. A process as claimed in claim 1, wherein the carbonyl dichloride is oxalyl chloride.

* * * * *